United States Patent [19]
Anlezark et al.

[11] Patent Number: 5,780,585
[45] Date of Patent: Jul. 14, 1998

[54] BACTERIAL NITROREDUCTASE FOR THE REDUCTION OF CB 1954 AND ANALOGUES THEREOF TO A CYTOTOXIC FORM

[75] Inventors: Gillian Anlezark; Roger Melton; Roger Sherwood, all of Salisbury; Thomas Connors, Carshalton; Frank Friedlos, Sutton; Michael Jarman, Sutton; Richard Knox, Sutton, all of United Kingdom; Anthony Mauger, Kensington, Md.; Caroline Joy Springer, Sutton, United Kingdom

[73] Assignee: Cancer Research Campaign Technology Limited, London, England

[21] Appl. No.: 504,047

[22] Filed: Jun. 7, 1995

Related U.S. Application Data

[62] Division of Ser. No. 232,018, Jul. 27, 1994, Pat. No. 5,633,158, filed as PCT/GB92/01947 Oct. 23, 1992.

[30] Foreign Application Priority Data

Oct. 23, 1991 [GB] United Kingdom ............... 9122464
Oct. 23, 1991 [GB] United Kingdom ............... 9122496

[51] Int. Cl.$^6$ ............... C07K 7/56; C07H 15/24; C07D 487/14; C07C 271/28; C07C 269/04; C07C 69/96; C07C 68/00
[52] U.S. Cl. ............... 530/317; 536/6.4; 548/422; 558/272; 558/275; 560/30; 560/32; 560/163
[58] Field of Search ............... 530/317; 536/6.4; 548/422; 558/272, 275; 560/30, 32, 163

[56] References Cited

U.S. PATENT DOCUMENTS

| | | | |
|---|---|---|---|
| 4,472,312 | 9/1984 | Anathasubramanian et al. | 552/298 |
| 4,617,398 | 10/1986 | Bardos et al. | 548/112 |
| 4,680,382 | 7/1987 | Sengupta . | |
| 4,868,303 | 9/1989 | Takase et al. | 544/357 |

FOREIGN PATENT DOCUMENTS

| | | |
|---|---|---|
| 0 317 956 | 5/1989 | European Pat. Off. . |
| 0320988 | 6/1989 | European Pat. Off. . |
| 0 330 432 | 8/1989 | European Pat. Off. . |
| 0 441 218 | 8/1991 | European Pat. Off. . |

OTHER PUBLICATIONS

Bryant, Christopher et al., "Cloning, Nucleotide Sequence, and Expression of the Nitroreductase Gene from *Enterobacter cloacae*", *Journal of Biological Chemistry*, vol. 266, No. 7, pp. 4126–4130 (Mar. 1991).

Bryant, D.W. et al., "Type I Nitroreductases of *Escherichia coli*", *Canadian Journal of Microbiology*, vol. 27, pp. 81–86 (1981).

Narai, Noriko et al., "A Comparative Study on 1-Nitro-pyrene and Nitrofurazone Reductases in *Escherichia Coli*" *J. Pharm. Dyn.*, vol. 7, pp. 407–413 (1984).

Doi, Takayoshi et al., "Properties of Nitrofuran Reductases from *Escherichia coliB/r*", *Chem.Pharm.Bull.*, vol. 31, pp. 1105–1107 (1983).

Chemical Abstracts, vol. 95, Abstract No. 98201a (1981), Mikhailopulo, I.A. et al., "Synthesis of glycosides on nicotinamide and nicotinamide mononucleotide."

Knox, Richard J., "A New Cytotoxic, DNA Interstrand Crosslinking Agent, 5-(Aziridin-1-YL)-4-Hydroxylamino-2-Nitrobenzamide, is Formed From 5-(Azirdin-1-YL)-2,4-Dinitrobenzamide (CB 1954) by a Nitroreductase Enzyme in Walker Carcinoma Cells", *Biochemical Pharmacology*, vol. 37, No. 24, pp. 4661–4669 (1988).

*Primary Examiner*—Michael G. Ambrose
*Attorney, Agent, or Firm*—Spencer & Frank

[57] ABSTRACT

A prodrug of the formula (I):

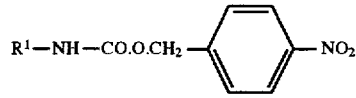

where $R^1$ is a group such that the compound R—$NH_2$ represents actinomycin D, doxorubicin, mitomycin C, or a nitrogen mustard of the formula (IV):

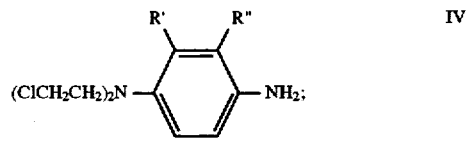

a prodrug of the formula (II):

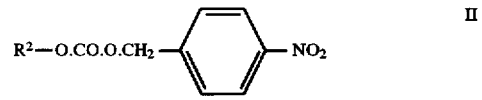

where $R^1$ is a group such that the compound $R^2OH$ is a phenolic nitrogen mustard; and processes whereby the prodrugs shown above are made in which a prodrug precursor compound is reacted with 4-nitrobenzyl chloroformate under anhydrous conditions.

8 Claims, 2 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1167 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Escherichia coli ( i x ) FEATURE:
        ( A ) NAME/KEY: CDS
        ( B ) LOCATION: 176..826

( x i ) SEQUENCE DESCRIPTION: SEQ ID NO:1:

```
TCGCGATCTG ATCAACGATT CGTGGAATCT GGTGGTTGAT GGTCTGGCTA AACGCGATCA          60

AAAAAGAGTG CGTCCAGGCT AAAGCGGAAA TCTATAGCGC ATTTTTCTCG CTTACCATTT         120

CTCGTTGAAC CTTGTAATCT GCTGGCACGC AAAATTACTT TCACATGGAG TCTTT ATG         178
                                                             Met
                                                              1

GAT ATC ATT TCT GTC GCC TTA AAG CGT CAT TCC ACT AAG GCA TTT GAT          226
Asp Ile Ile Ser Val Ala Leu Lys Arg His Ser Thr Lys Ala Phe Asp
             5                  10                  15

GCC AGC AAA AAA CTT ACC CCG GAA CAG GCC GAG CAG ATC AAA ACG CTA          274
Ala Ser Lys Lys Leu Thr Pro Glu Gln Ala Glu Gln Ile Lys Thr Leu
         20                  25                  30

CTG CAA TAC AGC CCA TCC AGC ACC AAC TCC CAG CCG TGG CAT TTT ATT          322
Leu Gln Tyr Ser Pro Ser Ser Thr Asn Ser Gln Pro Trp His Phe Ile
     35                  40                  45

GTT GCC AGC ACG GAA GAA GGT AAA GCG CGT GTT GCC AAA TCC GCT GCC          370
Val Ala Ser Thr Glu Glu Gly Lys Ala Arg Val Ala Lys Ser Ala Ala
 50                  55                  60                  65

GGT AAT TAC GTG TTC AAC GAG CGT AAA ATG CTT GAT GCC TCG CAC GTC          418
Gly Asn Tyr Val Phe Asn Glu Arg Lys Met Leu Asp Ala Ser His Val
```

|        |        |        |        |        |        |        |        |        |        |        |        |        |        |        |        |      |
|--------|--------|--------|--------|--------|--------|--------|--------|--------|--------|--------|--------|--------|--------|--------|--------|------|
|        |        |        |        | 70     |        |        |        |        | 75     |        |        |        |        | 80     |        |      |
| GTG    | GTG    | TTC    | TGT    | GCA    | AAA    | ACC    | GCG    | ATG    | GAC    | GAT    | GTC    | TGG    | CTG    | AAG    | CTG    | 466  |
| Val    | Val    | Phe    | Cys    | Ala    | Lys    | Thr    | Ala    | Met    | Asp    | Asp    | Val    | Trp    | Leu    | Lys    | Leu    |      |
|        |        |        | 85     |        |        |        |        | 90     |        |        |        |        | 95     |        |        |      |
| GTT    | GTT    | GAC    | CAG    | GAA    | GAT    | GCC    | GAT    | GGC    | CGC    | TTT    | GCC    | ACG    | CCG    | GAA    | GCG    | 514  |
| Val    | Val    | Asp    | Gln    | Glu    | Asp    | Ala    | Asp    | Gly    | Arg    | Phe    | Ala    | Thr    | Pro    | Glu    | Ala    |      |
|        |        | 100    |        |        |        |        | 105    |        |        |        |        | 110    |        |        |        |      |
| AAA    | GCC    | GCG    | AAC    | GAT    | AAA    | GGT    | CGC    | AAG    | TTC    | TTC    | GCT    | GAT    | ATG    | CAC    | CGT    | 562  |
| Lys    | Ala    | Ala    | Asn    | Asp    | Lys    | Gly    | Arg    | Lys    | Phe    | Phe    | Ala    | Asp    | Met    | His    | Arg    |      |
|        | 115    |        |        |        |        | 120    |        |        |        |        | 125    |        |        |        |        |      |
| AAA    | GAT    | CTG    | CAT    | GAT    | GAT    | GCA    | GAG    | TGG    | ATG    | GCA    | AAA    | CAG    | GTT    | TAT    | CTC    | 610  |
| Lys    | Asp    | Leu    | His    | Asp    | Asp    | Ala    | Glu    | Trp    | Met    | Ala    | Lys    | Gln    | Val    | Tyr    | Leu    |      |
| 130    |        |        |        | 135    |        |        |        |        | 140    |        |        |        |        |        | 145    |      |
| AAC    | GTC    | GGT    | AAC    | TTC    | CTG    | CTC    | GGC    | GTG    | GCG    | GCT    | CTG    | GGT    | CTG    | GAC    | GCG    | 658  |
| Asn    | Val    | Gly    | Asn    | Phe    | Leu    | Leu    | Gly    | Val    | Ala    | Ala    | Leu    | Gly    | Leu    | Asp    | Ala    |      |
|        |        |        |        | 150    |        |        |        |        | 155    |        |        |        |        | 160    |        |      |
| GTA    | CCC    | ATC    | GAA    | GGT    | TTT    | GAC    | GCC    | GCC    | ATC    | CTC    | GAT    | GCA    | GAA    | TTT    | GGT    | 706  |
| Val    | Pro    | Ile    | Glu    | Gly    | Phe    | Asp    | Ala    | Ala    | Ile    | Leu    | Asp    | Ala    | Glu    | Phe    | Gly    |      |
|        |        |        | 165    |        |        |        |        | 170    |        |        |        |        | 175    |        |        |      |
| CTG    | AAA    | GAG    | AAA    | GGC    | TAC    | ACC    | AGT    | CTG    | GTG    | GTT    | GTT    | CCG    | GTA    | GGT    | CAT    | 754  |
| Leu    | Lys    | Glu    | Lys    | Gly    | Tyr    | Thr    | Ser    | Leu    | Val    | Val    | Val    | Pro    | Val    | Gly    | His    |      |
|        |        | 180    |        |        |        |        | 185    |        |        |        |        | 190    |        |        |        |      |
| CAC    | AGC    | GTT    | GAA    | GAT    | TTT    | AAC    | GCT    | ACG    | CTG    | CCG    | AAA    | TCT    | CGT    | CTG    | CCG    | 802  |
| His    | Ser    | Val    | Glu    | Asp    | Phe    | Asn    | Ala    | Thr    | Leu    | Pro    | Lys    | Ser    | Arg    | Leu    | Pro    |      |
|        | 195    |        |        |        |        | 200    |        |        |        |        | 205    |        |        |        |        |      |
| CAA    | AAC    | ATC    | ACC    | TTA    | ACC    | GAA    | GTG    | TAATTCTCTC | | TTGCCGGGCA | | TCTGCCCGGC | | | | 856 |
| Gln    | Asn    | Ile    | Thr    | Leu    | Thr    | Glu    | Val    |        |        |        |        |        |        |        |        |      |
| 210    |        |        |        |        | 215    |        |        |        |        |        |        |        |        |        |        |      |

| | | | | |
|---|---|---|---|---|
| TATTTCCTCT | CAGATTCTCC | TGATTTGCAT | AACCCTGTTT | CAGCCGTCAT | CATAGGCTGC | 916 |
| TGTTGTATAA | AGGAGACGTT | ATGCAGGATT | TAATATCCCA | GGTTGAAGAT | TTAGCGGGTA | 976 |
| TTGAGATCGA | TCACACCACC | TCGATGGTGA | TGATTTTCGG | TATTATTTTT | CTGACCGCCG | 1036 |
| TCGTGGTGCA | TATTATTTTG | CATTGGGTGG | TACTGCGGAC | CTTCGAAAAA | CGTGCCATCG | 1096 |
| CCAGTTCACG | GCTTTGGTTG | CAAATCATTA | CCCAGAATAA | ACTCTTCCAC | CGTTTAGCTT | 1156 |
| TTACCCTGCA | G | | | | | 1167 |

( 2 ) INFORMATION FOR SEQ ID NO:2:

( i ) SEQUENCE CHARACTERISTICS:
        ( A ) LENGTH: 217 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Asp | Ile | Ile | Ser | Val | Ala | Leu | Lys | Arg | His | Ser | Thr | Lys | Ala | Phe |
| 1 | | | | 5 | | | | | 10 | | | | | 15 | |
| Asp | Ala | Ser | Lys | Lys | Leu | Thr | Pro | Glu | Gln | Ala | Glu | Gln | Ile | Lys | Thr |
| | | | 20 | | | | | 25 | | | | | 30 | | |
| Leu | Leu | Gln | Tyr | Ser | Pro | Ser | Ser | Thr | Asn | Ser | Gln | Pro | Trp | His | Phe |
| | | | 35 | | | | | 40 | | | | | 45 | | |
| Ile | Val | Ala | Ser | Thr | Glu | Glu | Gly | Lys | Ala | Arg | Val | Ala | Lys | Ser | Ala |
| | | 50 | | | | | 55 | | | | | 60 | | | |
| Ala | Gly | Asn | Tyr | Val | Phe | Asn | Glu | Arg | Lys | Met | Leu | Asp | Ala | Ser | His |
| 65 | | | | | 70 | | | | | 75 | | | | | 80 |
| Val | Val | Val | Phe | Cys | Ala | Lys | Thr | Ala | Met | Asp | Asp | Val | Trp | Leu | Lys |
| | | | | 85 | | | | | 90 | | | | | 95 | |

```
Leu  Val  Val  Asp  Gln  Glu  Asp  Ala  Asp  Gly  Arg  Phe  Ala  Thr  Pro  Glu
               100                 105                      110

Ala  Lys  Ala  Ala  Asn  Asp  Lys  Gly  Arg  Lys  Phe  Phe  Ala  Asp  Met  His
          115                 120                      125

Arg  Lys  Asp  Leu  His  Asp  Asp  Ala  Glu  Trp  Met  Ala  Lys  Gln  Val  Tyr
     130                 135                      140

Leu  Asn  Val  Gly  Asn  Phe  Leu  Leu  Gly  Val  Ala  Ala  Leu  Gly  Leu  Asp
145                      150                      155                      160

Ala  Val  Pro  Ile  Glu  Gly  Phe  Asp  Ala  Ala  Ile  Leu  Asp  Ala  Glu  Phe
               165                      170                      175

Gly  Leu  Lys  Glu  Lys  Gly  Tyr  Thr  Ser  Leu  Val  Val  Val  Pro  Val  Gly
               180                 185                      190

His  His  Ser  Val  Glu  Asp  Phe  Asn  Ala  Thr  Leu  Pro  Lys  Ser  Arg  Leu
          195                      200                      205

Pro  Gln  Asn  Ile  Thr  Leu  Thr  Glu  Val
     210                 215
```

( 2 ) INFORMATION FOR SEQ ID NO:3:

( i ) SEQUENCE CHARACTERISTICS:
        ( A ) LENGTH: 217 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Salmonella typhimurium ( x i ) SEQUENCE DESCRIPTION: SEQ ID NO:3:

```
Met  Asp  Ile  Val  Ser  Val  Ala  Leu  Gln  Arg  Tyr  Ser  Thr  Lys  Ala  Phe
1                   5                    10                       15

Asp  Pro  Ser  Lys  Lys  Leu  Thr  Ala  Glu  Glu  Ala  Asp  Lys  Ile  Lys  Thr
               20                   25                       30

Leu  Leu  Gln  Tyr  Ser  Pro  Ser  Ser  Thr  Asn  Ser  Gln  Pro  Trp  His  Phe
               35                   40                       45

Ile  Val  Ala  Ser  Thr  Glu  Glu  Gly  Lys  Ala  Arg  Val  Ala  Lys  Ser  Ala
     50                        55                       60

Ala  Gly  Asn  Tyr  Thr  Phe  Asn  Glu  Arg  Lys  Met  Leu  Asp  Ala  Ser  His
65                        70                   75                            80

Val  Val  Val  Phe  Cys  Ala  Lys  Thr  Ala  Asn  Asp  Asp  Ala  Trp  Leu  Glu
               85                        90                            95

Arg  Val  Val  Asp  Gln  Glu  Asp  Ala  Asp  Gly  Arg  Phe  Ala  Thr  Pro  Glu
               100                 105                      110

Ala  Lys  Ala  Ala  Asn  Asp  Lys  Gly  Arg  Arg  Phe  Phe  Ala  Asp  Met  His
          115                 120                      125

Arg  Val  Ser  Leu  Lys  Asp  Asp  His  Gln  Trp  Met  Ala  Lys  Val  Val  Tyr
     130                 135                      140

Leu  Asn  Val  Gly  Asn  Phe  Leu  Leu  Gly  Val  Ala  Ala  Met  Gly  Leu  Asp
145                      150                      155                      160

Ala  Val  Pro  Ile  Glu  Gly  Phe  Asp  Ala  Glu  Val  Leu  Asp  Ala  Glu  Phe
               165                      170                      175

Gly  Leu  Lys  Glu  Lys  Gly  Tyr  Thr  Ser  Leu  Val  Val  Val  Pro  Val  Gly
               180                 185                      190
```

| | | | | | | | | | | | | | | | |
|---|---|---|---|---|---|---|---|---|---|---|---|---|---|---|---|
| His | His | Ser | Val | Glu | Asp | Phe | Asn | Ala | Gly | Leu | Pro | Lys | Ser | Arg | Leu |
| | | 195 | | | | | 200 | | | | | 205 | | | |
| Pro | Leu | Glu | Thr | Thr | Leu | Thr | Glu | Val | | | | | | | |
| | 210 | | | | | 215 | | | | | | | | | |

(2) INFORMATION FOR SEQ ID NO:4:

(i) SEQUENCE CHARACTERISTICS:
      (A) LENGTH: 31 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
      (A) ORGANISM: Escherichia coli (xi) SEQUENCE DESCRIPTION: SEQ ID NO:4:

| | | | | | | | | | | | | | | |
|---|---|---|---|---|---|---|---|---|---|---|---|---|---|---|
| Met | Asp | Ile | Ile | Ser | Val | Ala | Leu | Lys | Arg | His | Ser | Thr | Lys | Ala | Phe |
| 1 | | | | 5 | | | | | 10 | | | | | 15 | |
| Asp | Ala | Ser | Lys | Xaa | Leu | Thr | Pro | Glu | Gln | Ala | Asp | Gln | Ile | Lys | |
| | | | 20 | | | | | 25 | | | | | 30 | | |

(2) INFORMATION FOR SEQ ID NO:5:

(i) SEQUENCE CHARACTERISTICS:
      (A) LENGTH: 41 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
      (A) ORGANISM: Escherichia coli (xi) SEQUENCE DESCRIPTION: SEQ ID NO:5:

| | | | | | | | | | | | | | | |
|---|---|---|---|---|---|---|---|---|---|---|---|---|---|---|
| Ala | Lys | Gln | Val | Tyr | Leu | Asn | Val | Gly | Asn | Phe | Leu | Leu | Gly | Val | Ala |
| 1 | | | | 5 | | | | | 10 | | | | | 15 | |
| Ala | Leu | Gly | Leu | Asp | Ala | Val | Pro | Ile | Glu | Gly | Phe | Asp | Ala | Ala | Ile |
| | | | 20 | | | | | 25 | | | | | 30 | | |
| Leu | Asp | Ala | Glu | Phe | Gly | Leu | Lys | Ile | | | | | | | |
| | | 35 | | | | | 40 | | | | | | | | |

BACTERIAL NITROREDUCTASE FOR THE REDUCTION OF CB 1954 AND ANALOGUES THEREOF TO A CYTOTOXIC FORM

CROSS-REFERENCE TO RELATED APPLICATION

This application is a division on U.S. application Ser. No. 08/232,018 filed Jul. 27, 1994, now U.S. Pat. No. 5,633,158, which is the United States National Stage of International Application No. 371 of PCT/GB92/01947, filed Oct. 23, 1992, the contents of which are incorporated herein by reference.

THIS INVENTION relates to the control of neoplastic tissue growth and is particularly concerned with the provision of new anti-tumour agents and with enzymes capable of converting prodrugs into anti-tumour agents.

The alkylating agent 5-(aziridin-1-yl)-2,4-dinitrobenzamide (hereinafter designated CB 1954) has been known, almost for 20 years, as an interesting experimental compound of unique selectivity. Although CB 1954 is structurally quite closely related to numerous other known alkylating agents which have a relatively broad range of activity, CB 1954 exhibits considerable activity against the Walker tumour cells in vivo or in vitro but was thought to be virtually inactive against other tumours.

It was recently discovered that the selectivity of CB 1954 arose from the fact that it was not an anti-tumour agent per se but was a prodrug for an anti-tumour agent generated from CB 1954 by a nitroreductase enzyme found in the Walker cell. This nitroreductase from the Walker cell was subsequently shown to be an enzyme known from other sources which was an NAD(P)H dehydrogenase (quinone) classified as EC.1.6.99.2, see Robertson et al. J. Biol. Chem. 261, 15794–15799 (1986).

In the course of the previous investigations with CB 1954, it was found that the Walker cell enzyme EC.1.6.99.2 had the ability to reduce the 4-nitro group of CB 1954 to the corresponding hydroxylamine and that it was the resulting 5-(aziridin-1-yl)-2-nitro-4-hydroxylamino-benzamide that was the active anti-tumour agent.

The use of prodrugs represents a clinically very valuable concept in cancer therapy since, particularly where the prodrug is to be converted to an anti-tumour agent under the influence of an enzyme that is linkable to a monoclonal antibody that will bind to a tumour associated antigen, the combination of such a prodrug with such an enzyme monoclonal/antibody conjugate represents a very powerful clinical agent.

We have now discovered new nitroreductases, obtainable from bacterial sources, that are of interest in that not only are they capable of converting CB 1954 into an active anti-tumour agent, but also, unlike EC.1.6.99.2, capable of converting CB 1954 analogues which are also prodrugs into active anti-tumour agents.

Figure 1:
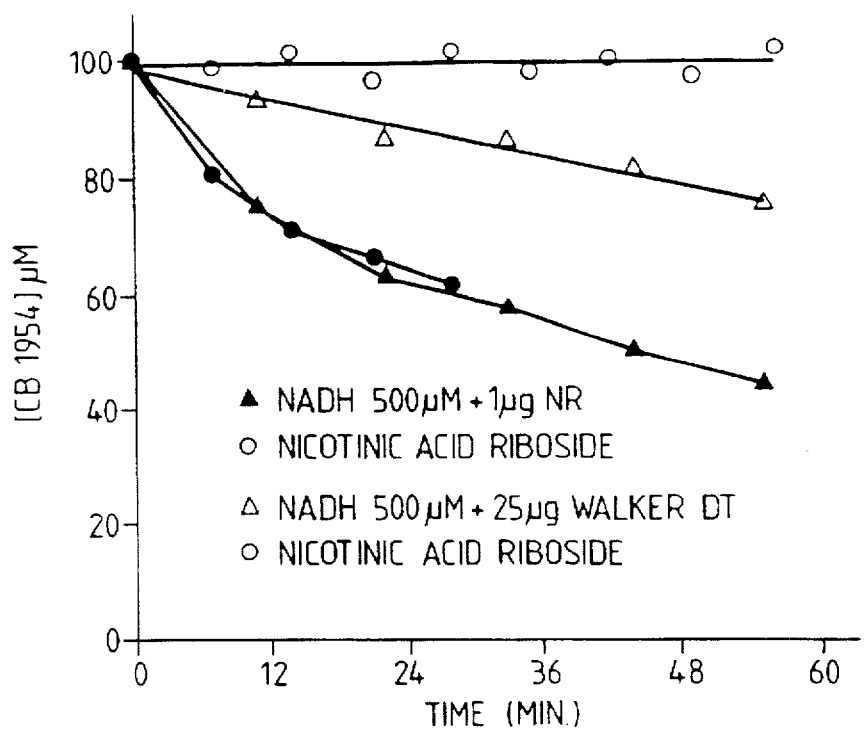
FIG. 1 shows the results of an experiment in which CB 1954 (100 μM) and reduced cofactor (500 μM) were incubated with enzyme (2 mg/ml) E. coli nitroreductase (A) or 25 μg/ml Walker DT diaphorase (B) in 10 mM sodium phosphate buffer (pH7) in air at 37° C. At various times aliquots (10 μl) were injected onto a Partisil SCX (240×4.7 mm) HPLC column and eluted isocratically (2 ml/min) with 100 mM $NaH_2PO_4$. The eluate was continuously monitored for absorption at 320, 260 and 360 nm and the concentration of CB 1954 calculated by integration of the peak corresponding to this compound on the HPLC trace.

The present invention provides a nitroreductase, obtainable from a bacterium having the following characteristics as exemplified by examples isolated from *Escherichia coli* B and *Bacillus amyloliquifaciens*:

1. It is a flavoprotein having a molecular weight in the range 20–60 Kilodaltons;
2. It requires either NADH or NAD(P)H or analogues thereof as a cofactor.
3. It has a Km for NADH or NAD(P)H in the range 1–100 μM.
4. It is capable of reducing either or both nitro groups of CB 1954 and analogues thereof to a cytotoxic form e.g. the hydroxylamine.

The nitroreductases of the invention occur naturally within the cells of *E. coli* B, *E. coli* C and other *E. coli* strains e.g. K12 type as well as other gram negative organisms e.g. *Thermus aquaticus*, and gram positive bacteria such as *Bacillus amyloliquifaciens* and *Bacillus caldotenax*. They can be recovered from such cells by disrupting the cells and subjecting the cell contents to chromatographic separation and isolating the nitroreductase.

For example, the nitroreductase of the present invention from *E. coli* B has been purified to homogeneity—see Table 1 and has been subjected to amino acid sequence analysis with the results set out in Table 2. The upper sequence shows the deduced amino acid sequence of the 219-mer nitroreductase obtained from *Salmonella typhimurium* as described by Watanabe et al. Nucl. Acids. Res. 18, 1059 (1990). The lower sequence in bold type shows the sequence of the cyanogen bromide fragments of the *E. coli* B nitroreductase as an example of the present invention showing a certain degree of homogeneity but sufficient differences to confirm that it is nitroreductase that is different from that of Watanabe et al and the recently described *Enterobacter cloacae* nitroreductases, see Bryant et al. J. Biol Chem. 266, 4126 (1991) or the Walker cell nitroreductase and is a previously unreported enzyme.

The amino acid sequence of the *E. coli* B nitroreductase of the invention can also been derived from sequencing the nucleotides in the nitroreductase gene and these sequences are set out below in Table 3. The nucleotide sequence of Table 3 has been used to prepare the attached sequence listings.

Using the information in Table 3, a nitroreductase according to the present invention may be prepared by expressing DNA encoding the nitroreductase in a suitable expression vector contained in a host cell, and recovering the nitroreductase. The expression vector may be, for example, a bacterial, yeast, insect or mammalian expression vector and the host cell will be selected to be compatible with the vector.

As indicated above, the new enzymes of the present invention are capable of reducing a nitro group in various substrate molecules and we have found that the enzymes are particularly useful in their ability to reduce the nitro group of various p-nitrobenzyloxycarbonyl derivatives of cytotoxic compounds to give "self-immolative" compounds that automatically decompose to release cytotoxic compounds.

The interest in the present approach resides in the fact that the cytotoxicity of various cytotoxic compounds containing amino or hydroxy substituents, particularly aromatic amino or hydroxy substituents give rise to p-nitrobenzyloxycarbonyl derivatives of the amino or hydroxy group which exhibit considerably less cytotoxicity than the amino or hydroxy parent compound. Thus, it is possible to use the p-nitrobenzyloxycarbonyl derivatives as prodrugs in a system of the type discussed above where the prodrug is converted into an anti-tumour agent under the influence of an enzyme that is linkable to a monoclonal antibody that will bind to the tumour associated antigen.

Accordingly, the present invention provides new compounds of the general formula:

$R^1$—NH—CO.O.CH$_2$—〈benzene〉—NO$_2$    I and:

$R^2$—O.CO.O.CH$_2$—〈benzene〉—NO$_2$    II where $R^1$ and $R^2$ are groups such that the compound $R^1NH_2$ and $R^2OH$ are cytotoxic compounds.

It is preferred that compounds $R^1NH_2$ and $R^2OH$ are aromatic cytotoxic compounds and the compounds $R^1NH_2$ can be any one of the well known nitrogen mustard compounds, for example based on p-phenylene diamine. Thus, the compound $R^1NH_2$ can be:

(ClCH$_2$CH$_2$)$_2$N—〈benzene〉—NH$_2$    III or analogues of this compound with the general structure IV (ClCH$_2$CH$_2$)$_2$N—〈benzene with R' and R''〉—NH$_2$    IV where R' and R'' are H, F or CH$_3$, and particularly where R'=H and R''=CH$_3$;

or

R'=CH$_3$ and R''=H;

or

R'=H and R''=F;

or

R'=F and R''=H.

A further type of amino cytotoxic compound that can be used in accordance with the present invention are compounds such as actinomycin D, doxorubicin, daunomycin and mitomycin C. The structure of the pro-drugs derived from actinomycin D, doxorubicin and mitomycin C are shown below as V, VI and VII respectively.

[Structure V: actinomycin D derivative with MeVal-Sar-Pro-D-Val-Thr-(O) peptide chains]

[Structure VI: doxorubicin derivative]

[Structure VII: mitomycin C derivative]

Similar p-nitrobenzyloxy derivatives can be made at the amino substituent of other actinomycins and of the other cytotoxic compounds of the type mentioned above.

In addition to forming p-nitrobenzyloxycarbonyl derivatives at an amino group on a cytotoxic compound, similar derivatives can be made at a hydroxy group, particularly a phenolic hydroxy group of a cytotoxic compound. Here, attention is directed at the phenolic nitrogen mustard compounds, and a specific compound of the invention of this type is of the formula:

(ClCH$_2$CH$_2$)$_2$N—〈benzene〉—O.CO.O.CH$_2$—〈benzene〉—NO$_2$    VIII

The new enzymes of the present invention are capable not only of reducing at least one of the nitro groups of CB 1954 but also at least ore of the nitro groups of certain CB 1954 analogues, e.g. descarboxamido CB1954 (1-aziridin-1-yl-2, 4-dinitrobenzamide—known as CB 1837) and N,N-dimethyl CB 1954 [N,N-dimethyl-(5-aziridin-1-yl-2,4-dinitrobenzamide also known as CB 10-107]. The new enzymes of the present invention are also capable of reducing the nitro groups of other aromatic nitro compounds such as 5-chloro-2,4-dinitrobenzamide, 3,5-dinitrobenzamide, 3-nitrobenzamide, 4-nitrobenzamide and 5-nitro-2-furaldehydesemicarbazone (nitrofurazone).

The present invention also provides hydroxylamino derivatives of the general formula X:

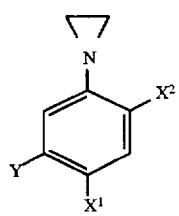

wherein $X^1$ and $X^2$, which may be the same or different, are each $NHOR^5$ or $NO_2$ with the proviso that $X^1$ and $X^2$ are not both $NO_2$, here $R^5$ is H or a carboxylic acyl or hydrocarbyl group as defined above in relation to formula IX and Y is H or $CON(CH_3)_2$. In the compounds of formula X containing two hydroxylamino groups, the group R can be the same or different but will normally be the same.

As mentioned above, the new p-nitrophenylbenzyloxy compounds of the invention of formulae I and II are of interest in that they have a reduced cytotoxicity compared to that of the cytotoxic compound $R^1NH_2$ or $R^2OH$ from which they are derived and they are capable of acting as a substrate for the nitroreductase of the present invention. While the present invention is not dependent, for its definition, upon the exact mode of action of the nitroreductase on the compound of formula I or II, it is believed that the nitro group of the p-nitrophenyl-benzyloxycarbonyl residue is converted to the corresponding amino or hydroxylamino group and that the resulting p-aminobenzyloxycarbonyl or p-hydroxyl-aminobenzyloxycarbonyl compound automatically degrades under the reaction conditions used for the enzymatic reduction to release the cytotoxic compound and form p-aminobenzyl alcohol or p-hydroxylaminobenzyl alcohol and carbon dioxide as by products in accordance with the following reaction scheme:

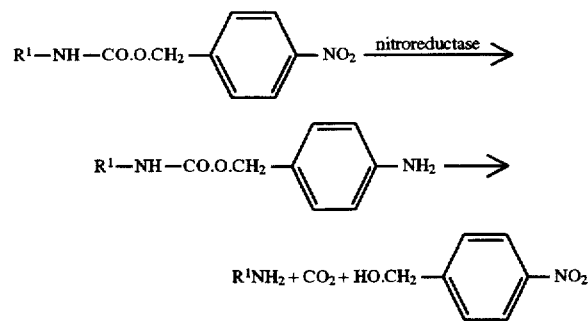

The p-nitrobenzyloxycarbonyl compounds of the invention are conveniently prepared by methods of chemical synthesis known per se. For example, the amine or hydroxy cytotoxic compounds can be reacted with 4-nitrobenzyl chloroformate under anhydrous conditions in the presence of a hydrogen chloride acceptor, particularly an alkylamine such as triethylamine. This reaction can be carried out in a dry organic solvent such as chloroform and the resulting compound of the invention of formula I or formula II isolated from the organic solvent by conventional methods such as chromatography.

The new compounds of the present invention IX and X will normally be prepared by subjecting the corresponding dinitro compound to the action of the new nitroreductase of the present invention. It is, of course, also possible to produce the new compounds of the present invention IX and X by chemical synthesis, using selective reducing agents followed by conversion of the resulting hydroxylamine to its corresponding ester or ether. The esters and ethers are more conveniently prepared semi-synthetically by carrying out the reduction of the nitro group with the nitroreductase of the present invention to give the corresponding hydroxylamine that is then converted by known chemical methods to the corresponding ester or ether.

One of the most convenient ways of producing the new nitroreductase of the invention is to recover the material from the cell contents of bacteria such as *E. coli* B. Alternatively, it is possible to clone the gene, isolatable from the bacteria, encoding the desired enzyme and to transfer the cloned gene, in a suitable vector system, into another host cell from which or in which it can be expressed.

In order to bring about the enzymatic reduction of CB 1954 and its analogues with the new enzymes of the present invention, it is necessary to have a cofactor present in the reaction system. The ability of the enzyme of the present invention to bring about this reduction can be demonstrated experimentally by the use of NADH or NAD(P)H as the cofactor but the use of such cofactors in clinical practice may be problematic in view of the ease with which NAD (P)H particularly is oxidised by other enzymes present in the body and the lack of selectivity of the cofactors between the various mammalian and non-mammalian enzymes. We have now found that the riboside of 1,4-dihydronicotinic acid is as least as effective as a cofactor in the nitroreductase reduction of CB 1954 and analogues thereof and moreover, because of its selectivity to the *E. coli* nitroreductase of the invention, is more suited to clinical use which makes its incorporation in a multi-component system of the type described below particularly valuable.

The riboside of 1,4-dihydro-nicotinic acid which can be used in the present invention as a cofactor is a new compound and forms part of the present invention. It can be prepared from commercially available nicotinic acid ribotide which is first converted to the corresponding riboside by enzymatic dephosphorylation e.g. using an alkaline phosphatase. The riboside, obtained by such enzymatic dephosphorylation, or by chemical synthesis, using the method described by Jarman, J. Chem. Soc. (c) 918–920 (1969) can then be reduced, e.g. using an alkali metal hydrosulphite, to give 1,4-dihydro-nicotinic acid riboside.

One of the most important practical applications of the new enzymes of the present invention is that they can be used in association with nitro compounds that are prodrugs for anti-tumour agents and so provide a system of cancer chemotherapy where the extent of exposure of the patient to the cytotoxic agent is limited, so far as possible, to those regions where there is the interaction between the prodrug and the nitroreductase of the invention. Thus, one aspect of the present invention is to provide a method of chemotherapy and a system for chemotherapy involving the conjoint use of the nitroreductase of the present invention in association with a nitro compound which is a prodrug for a cytotoxic compound.

The most or one of the most convenient ways of utilising the system of the present invention is to conjugate the nitroreductase of the present invention to a targeting agent such as a monoclonal antibody that will bind with a tumour-associated antigen.

As used herein, the term "monoclonal antibody" will be understood by those of skill in the art not simply to refer to antibodies produced by traditional hybridoma techniques, but also to cover antibodies and variants thereof produced by recombinant means. These include, for example, humanised antibodies such as those with a constant region from a human antibody grafted onto a non-human antibody variable region (see for example EP-A-0 120 694), chimeric antibodies such as those with non-human complementarity determining regions (CDRs) grafted into a human variable region framework (see for example EP-A-0 239 400) and single chain antibodies. Fragments of such monoclonal antibodies which retain their target binding activity are also included by the general term "monoclonal antibody". This includes Fab' and F(ab')$_2$ fragments.

The selection of monoclonal antibody will clearly be influenced by the nature of the target tumour but for the purposes of illustrating the present invention, reference may be made to the anti-CEA antibody $A_5B_7$.

As an alternative to the use of a monoclonal antibody, it is also envisaged that other targeting agents to which the nitroreductase of the present invention is conjugated may be used. For example, it is known that certain soluble macromolecules can be used for passive tumour targeting of certain tumour types. Many solid tumours possess vasculature that is hyperpermeable to macromolecules. Although the reasons for this are not clearly understood, the result is that such tumours can selectively accumulate circulating macromolecules. The enhanced permeability and retention effect (EPR effect) is thought to constitute the mechanism of action of SMANCS (styrene/maleic-anhydride-neocarzinostatin), now in regular clinical use in Japan for the treatment of hepatoma. Another class of conjugates under investigation for anticancer activity is N-(2-hydroxypropyl)methacrylamide copolymer-anthracycline conjugates (L. Seymour, Critical Reviews in Therapeutic Drug Carrier Systems, 9(2) 135–187 (1992)). Thus, conjugates of a polymer, including styrene/maleic-anhydride or N-(2-hydroxy-propyl)methacrylamide copolymer, and the nitroreductase of the invention can be used place of conjugates of a monoclonal antibody and enzyme.

With this system, it is possible in a course of cancer chemotherapy to administer to the patient requiring the treatment the nitro compound which is the prodrug for the cytotoxic compound and the enzyme/targeting agent conjugate. The prodrug and the conjugate can be administered simultaneously but it is often found preferable, in clinical practice, to administer the enzyme/agent conjugate before the prodrug, e.g. up to 72 hours before, in order to give the enzyme/agent conjugate an opportunity to localise in the region of the tumour target. By operating in this way, when the prodrug is administered, conversion of the prodrug to the cytotoxic agent tends to be confined to the regions where the enzyme/agent conjugate is localised, i.e. the region of the target tumour and damage to healthy cells caused by the premature release of the cytotoxic agent is minimised.

The degree of localisation of the enzyme/agent conjugate (in terms of the ratio of localized to freely circulating active conjugate) can be further enhanced using the clearance and/or inactivation systems described in WO89/10140. This involves, usually following administration of the conjugate and before administration of the prodrug, the administration of a component (a "second component") which is able to bind to the such part of the conjugate so as to inactivate the enzyme and/or accelerate the clearance of the conjugate from the blood. Such a component may include an antibody to the nitroreductase of the invention which is capable of inactivating the enzyme.

The second component may be linked to a macromolecule such as dextran, a liposome, albumin, macroglobulin or a blood group O erythrocyte so that the second component is restrained from leaving the vascular compartment. In addition or as an alternative, the second component may include a sufficient number of covalently bound galactose residues, or residues of other sugars such as lactose or mannose, so that it can bind the conjugate in plasma but be removed together with the conjugate from plasma by receptors for galactose or other sugars in the liver. The second component should be administered and designed for use such that it will not, to any appreciable extent, enter the extravascular space of the tumour where it could inactivate localised conjugate prior to and during administration of the prodrug.

The exact dosage regime will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of both the prodrug and the enzyme/agent conjugate and administration by the intravenous route is frequently found to be the most practical.

Bearing in mind the manner in which the enzymes of the present invention are to be used, the present invention extends to pharmaceutical compositions comprising the enzyme, preferably conjugated to a targeting agent such as a monoclonal antibody capable of binding to a tumour-associated antigen in association with a pharmaceutically acceptable carrier or diluent, normally one suitable for parenteral administration.

The present invention also extends to pharmaceutical compositions comprising one or more of the p-nitrobenzyloxycarbonyl compounds of the present invention of formula I, formula II, formula V, formula VI or formula VII in association with a pharmaceutically acceptable carrier or diluent, normally one for parenteral administration.

The present invention further extends to pharmaceutical compositions comprising the hydroxylamino anti-tumour agents of the present invention of formula IX or formula X in association with a pharmaceutically acceptable carrier or diluent, normally one for parenteral administration.

The present invention also provides a system for use in the control of neoplasia in a human or animal subject comprising the nitroreductases of the present invention, preferably conjugated with a targeting agent such as monoclonal antibody that will bind to a tumour-associated antigen, in association with at least one of a p-nitrobenzyloxycarbonyl compound of Formula I, II, V, VI or VII which is a prodrug for an anti-tumour agent and preferably a riboside or ribotide of nicotinic acid or nicotinamide to act as a cofactor for the enzyme. The present invention extends to a method of treating neoplasia in a human or animal host requiring such treatment which comprises administering to the host an effective amount of a p-nitrobenzyloxycarbonyl compound of Formula I, II, V, VI or VII which is a prodrug for an anti-tumour agent and the enzyme of the present invention, preferably conjugated with a targeting agent such as a monoclonal antibody that will bind to a tumour-associated antigen, the enzyme preferably being used in association with an ribotide or riboside of nicotinic acid or nicotinamide as cofactor for the enzyme.

The present invention further provides a system for use in the control of neoplasia in a human or animal subject comprising a nitroreductase of the present invention, preferably conjugated with a targeting agent such as a monoclonal antibody that will bind to a tumour-associated antigen, in association with a nitro compound which is a prodrug for an anti-tumour agents of the formula IX or X and preferably a riboside or ribotide of nicotinic acid or nicotinamide to act as a cofactor for the enzyme. The present invention also provides a method of treating neoplasia in a human or animal host requiring such treatment which comprises administering to the host an effective amount of a nitro compound which is a prodrug for an anti-tumour agents of the formula IX or X and the enzyme of the present invention, preferably conjugated with a targeting agent such as a monoclonal antibody that will bind to a tumour-associated antigen, the enzyme preferably being used in association with an ribotide or riboside of nicotinic acid or nicotinamide as cofactor for the enzyme.

The various systems for use in the treatment of neoplasia described above optionally include the "second component" for accelerated clearance described above. Likewise, the methods of treatment of neoplasia described above optionally include as part of that method the use of the second component, an effective amount of which is administered after administration of the enzyme, in order to increase the ratio of localised to freely circulating enzyme. Reference may be made to WO89/10140 for further particular details of the second component, and such details can be incorporated for use in the present invention.

The present invention is further illustrated by the following Examples.

EXAMPLE I

Isolation and purification of a nitroreductase enzyme from E. coli B.

200 grams of E. coli B cell paste were resuspended to a total volume of 1 liter of 20 nM potassium phosphate buffer, pH 7, containing 0.3M ammonium sulphate. The cells were broken ultrasonically using an MSE Soniprep 150 disintegrator (3×30 seconds on full power with 60 second intervals to allow heat to dissipate). To aid clarification of the extract, DNase (23,000 Kunitz units/L) and RNase (2,400 Kunitz units/L) were added prior to centrifugation at 8,000 g for 30 minutes to remove cell debris. The clear yellowish supernatant was passed through a 0.45 μm filter prior to chromatography.

The filtered extract was applied to a column (25×5 cm) of Phenyl-Sepharose CL-6B (Pharmacia) in 20 mM potassium phosphate buffer, pH 7, containing 0.3M ammonium sulphate. After washing with 2 column volumes of starting buffer, the column was eluted with 10 mM Tris-HCl buffer, pH 7.6. Active fractions were pooled and dialysed for 18 hours against 20 mM Tris-HCl, pH 7.6, to remove traces of ammonium sulphate. The dialysed fractions were applied in 50 ml aliquots to Q-Sepharose-High Performance in 20 mM Tris-HCl, pH 7.6, at a flow rate of 4 ml per minute. Elution was by a 0–0.2M gradient of KCl, the nitroreductase eluting at 0.1–0.12M KCl. Active fractions were pooled and desalted into 20 mM Bis Tris propane, pH 7, using a column (32×6 cm) of Sephadex G25 medium. These fractions were applied to Q-Sepharose High Performance (Hi-Load 26/10 column, Pharmacia) equilibrated in 20 mM Bis Tris propane, pH7. Elution was by a 0–0.1M gradient of KCl. Nitroreductase eluted as the first major peak at 0.07–0.09M KCl.

Homogeneity of the final product was ascertained using precast 8–25% gradient gels for native polyacrylamide gel electrophoresis (Pharmacia Phastsystem). Electrophoresis was performed for 75 vh.

The nitroreductase in crude and partially purified fractions was routinely assayed by its quinone reductase activity using menadione as substrate, NADH as co-factor and cytochrome C as terminal electron acceptor.

Determination of Isoelectric Point

The isoelectric point of nitroreductase was determined by isoelectric focusing (Pharmacia Phastsystem, focusing for 400 vh) and chromatofocusing using a Mono P column (Pharmacia Mono P HR5/20, 20 mM Bis-Tris pH 6.3 and polybuffer 74, pH 4.0).

The E. coli nitroreductase was isolated as a pure protein with a molecular weight of 24 kDa (as determined by both SDS-polyacrylamide gel electrophoresis and gel filtration chromatography). A second protein, which had quinone reductase activity but was inactive as a nitroreductase against CB 1954, partially co-elutes from Phenyl Sepharose and can be fully separated from the active enzyme by the ion exchange chromatography step on Q-Sepharose high performance (see Table 1) at pH 7.6. The two enzymes differ in molecular weight (inactive 55 KDa; active 24 KDa) and isoelectric point (inactive 5.2; active 5.1). The active protein has a yellow coloration suggesting the presence of a flavin coenzyme. After heating at 70° C. for 20 minutes this flavin could be separated from the apoenzyme by ultrafiltration and shown to be FMN, rather than FAD, using HPLC.

TABLE 1

The purification of a nitroreductase from E. coli B. The enzyme activity was assayed, at 37° C., by its quinone reductase activity using menadione (10 μM) as substrate, NADH (500 μM) as cofactor and cytochrome C (70 μM) as terminal electron acceptor. A unit was defined as 1 μmole of cytochrome C reduced per minute.

| FRACTION | | TOTAL ACTIVITY (Units) | SPECIFIC ACTIVITY (Units/mg protein) | YIELD (%) | |
|---|---|---|---|---|---|
| Crude | | 3784* | 0.34 | 100 | |
| Phenyl Sepharose | | 2371* | 1.6 | 63 | |
| | | CB 1954 | | CB 1954 | CB 1954 |
| | CB 1954 | CB 1954 | | ACTIVE | INACTIVE |
| | ACTIVE | INACTIVE | | | |
| | 1109 | 1262 | | 30 | 33 |
| Q-Sepharose (Tris, pH7.6) | 666 | — | 79 | 18 | — |
| Q-Sepharose (Bis-Tris propane, PH7) | 310 | — | 130 | 8 | — |

*This includes activity from enzymes not active against CB 1954

Fragments suitable for sequence analysis were produced by digestion of the enzyme with cyanogen bromide. The peptides which resulted from these digests were purified by reverse-phase HPLC, using a RP 300 column (25×4.6 mm) (Brownlee) and a solvent gradient of 10–60% acetonitrile in water with 0.06% trifluoroacetic aid in each solvent. Sequence analysis was performed by automated Edman degradation using an Applied Biosystems 470A gas phase protein sequencer (Kelvin Close, Warrington, U.K.).

Amino acid sequence analysis of the nitroreductase

The *E. coli* nitroreductase as isolated above was subject to amino acid sequence analysis. In contrast to the enzyme isolated from the Walker tumour, EC.1.6.99.2, the nitroreductase of the present invention was not blocked at the N-terminus and gave a clear N-terminal sequence of 31 amino acid residues (SEQ ID NO: 4) and a peptide, generated by digestion with cyanogen bromide, of a further 41 residues (SEQ ID NO: 5). These partial sequences are given in Table 2.

sis of both strands. In Table 3 is shown the nucleotide sequence of 1167 base NruI/Pst fragment which contains an open reading frame of 651 nucleotides encoding the nitroreductase (SEQ ID NO: 1). Putative sequence of Shine-Delgarno and transcriptional termination signal are indicated.

TABLE 2

Amino acid sequences of the N-terminus of the *E. coli* B nitroreductase (SEQ ID NO: 4) and of a peptide (SEQ ID NO: 5) obtained after digestion of the nitroreductase with cyanogen bromide (bold type) and a comparison with the deduced protein sequence of the nitroreductase from *Salmonella typhimurium* (SEQ ID NO: 3) (Watanabe et al. 1990).

```
1                   10                  20                      30
M D I V S V A L Q R Y S T K A F D P S K K L T   A E E A   D K I K T L
M D I I S V A L K R H S T K A F D A S K - L T (P) E Q A (D) Q I K 40                  50                  60
L Q Y S P S S T N S Q P W H F I V A S T E E G K A R V A K S A A G N Y 70                  80                  90                  100
T F N E R K M L D A S H V V V F C A K T A N D D A W L E R V V D Q E D 110                 120                 130
A D G R F A T P E A K A A N D K G R R F F A D M H R V S L K D D H Q W 140                 150                 160                 170
M   A K V V Y L N V G N F L L G V A A M G L D A V P I E G F D A E V L
(M) A K Q V Y L N V G N F L L G V A A L G L D A V P I E G F D A A I L 180                 190                 200
D A E F G L K E K G Y T S L V V V P V G H H S V E D F N A G L P K S R
D A E F G L K I 210             219
L P L E T T L T E V
```

Nucleotide sequence of the nitroreductase gene

The nitroreductase gene of *E. coli* has been cloned and its nucleotide sequence determined by dideoxy sequence analy-

TABLE 3

<u>NruI</u>
<u>TCGCGA</u>TCTGATCAACGATTCGTGGAATCTGGTGGTTGATGGTCTGGCTAAACGCGATCA  60

AAAAAGAGTGCGTCCAGGCTAAAGCGGAAATCTATAGCGCATTTTTCTCGCTTACCATTT  120

S.D.
CTCGTTGAACCTTGTAATCTGCTGGCACGCAAAATTACTTTCACA<u>TGGAGT</u>CTTTATGGA  180
                                                                                                                                        m  d

TATCATTTCTGTCGCCTTAAAGCGTCATTCCACTAAGGCATTTGATGCCAGCAAAAAACT  240
 i  i  s  v  a  l  k  r  h  s  t  k  a  f  d  a  s  k  k  l

TACCCCGGAACAGGCCGAGCAGATCAAAACGCTACTGCAATACAGCCCATCCAGCACCAA  300
 t  p  e  q  a  e  q  i  k  t  l  l  g  y  s  p  s  s  t  n

CTCCCAGCCGTGGCATTTTATTGTTGCCAGCACGGAAGAAGGTAAAGCGCGTGTTGCCAA  360
 s  q  p  w  h  f  i  v  a  s  t  e  e  g  k  a  r  v  a  k

ATCCGCTGCCGGTAATTACGTGTTCAACGAGCGTAAAATGCTTGATGCCTCGCACGTCGT  420
 s  a  a  g  n  y  v  f  n  e  r  k  m  l  d  a  s  h  v  v

GGTGTTCTGTGCAAAAACCGCGATGGACGATGTCTGGCTGAAGCTGGTTGTTGACCAGGA  480
 v  f  c  a  k  t  a  m  d  d  v  w  l  k  l  v  v  d  q  e

AGATGCCGATGGCCGCTTTGCCACGCCGGAAGCGAAAGCCGCGAACGATAAAGGTCGCAA  540
 d  a  d  g  r  f  a  t  p  e  a  k  a  a  n  d  k  g  r  k

TABLE 3-continued

```
                BglII
GTTCTTCGCTGATATGCACCGTAAAGATCTGCATGATGATGCAGAGTGGATGGCAAAACA  600
 f   f   a   d   m   h   r   k   d   l   h   d   d   a   e   w   m   a   k   q

GGTTTATCTCAACGTCGGTAACTTCCTGCTCGGCGTGGCGGCTCTGGGTCTGGACGCGGT  660
 v   y   l   n   v   g   n   f   l   l   g   v   a   l   g   l   d   a   v

ACCCATCGAAGGTTTTGACGCCGCCATCCTCGATGCAGAATTTGGTCTGAAAGAGAAAGG  720
 p   i   e   g   f   d   a   a   i   l   d   a   e   f   g   l   k   e   k   g

CTACACCAGTCTGGTGGTTGTTCCGGTAGGTCATCACAGCGTTGAAGATTTTAACGCTAC  780
 y   t   s   l   v   v   v   p   v   g   h   h   s   v   e   d   f   n   a   t

GCTGCCGAAATCTCGTCTGCCGCAAAACATCACCTTAACCGAAGTGTAATTCTCTCTTGC  840
 l   p   k   s   r   l   p   q   n   i   t   l   t   e   v   .

terminator
CGGGCATCTGCCCGGCTATTTCCTCTCAGATTCTCCTGATTTGCATAACCCTGTTTCAGC  900

CGTCATCATAGGCTGCTGTTGTATAAAGGAGACGTTATGCAGGATTTAATATCCCAGGTT  960

GAAGATTTAGCGGGTATTGAGATCGATCACACCACCTCGATGGTGATGATTTTCGGTATT  1020

ATTTTTCTGACCGCCGTCGTGGTGCATATTATTTTGCATTGGGTGGTACTGCGGACCTTC  1080

GAAAAACGTGCCATCGCCAGTTCACGGCTTTGGTTGCAAATCATTACCCAGAATAAACTC  1140

PstI
TTCCACCGTTTAGCTTTTACCCTGCAG  1167
```

EXAMPLE 2

Enzymatic reduction of CB 1954

CB 1954 (100 µM and also containing [U-$^3$H] CB 1954 at 1.6×10$^5$ dpm per nmole), NADH or NAD(P)H (500 µM) were incubated with the active enzyme obtained as described in Example 1, (generally 2 µg/ml E. coli nitroreductase or 35 µg/ml Walker NAD(P)H dehydrogenase (quinone) EC 1.6.99.2) in 10 nM sodium phosphate buffer (pH 7) under either air or helium. At various times aliquots (10 µl) were injected onto a Partisphere SCX (110×4.7 mm) HPLC column and eluted isocratically (2 ml/min) with 100 mM NaH$_2$PO$_4$.

The eluate was continuously monitored for adsorption at 310, 260 and 360 nm and the spectra of eluting components recorded using a diode-array detector. Samples (0.5 ml) were collected and the tritium activity of each determined by liquid scintillation counting. This separation system could resolve all the expected reduction products.

To confirm further the identity of any reduction products, the above reduction mixture was also injected onto an ODS-5 reverse phase HPLC column and eluted (1 ml/min) with a methanol gradient (0–30% linear over 30 min, 30–100% linear over 10 min.) in 0.1M sodium phosphate buffer (pH 7).

Reduction of CB 1954 by the E. coli nitroreductase resulted in the formation of two products, shown to be, by comparison of retention times and spectral characteristics with known standards, 5-(aziridin-1-yl)-4-hydroxylamino-2-nitrobenzamide and 5-(aziridin-1-yl)-2-hydroxylamino-4-nitrobenzamide. No other CB 1954 metabolites were found. In further confirmation of the formation of both the 2 and the 4-hydroxylamines by the nitroreductase of the invention, 33 µM of 4-hydroxylamine was formed when 67 µM of CB 1954 was reduced by the nitroreductase. In contrast 50 µM of 4-hydroxylamine was formed by the reduction of 50 µM of CB 1954 by the Walker NAD(P)H dehydrogenase (quinone). Based on initial rates of 4-hydroxylamine formation nitroreductase is 31.2 fold more active per mg protein than NAD(P)H dehydrogenase (quinone) (or 62 fold more active by CB 1954 reduction) under the standard conditions used.

The rate of reduction of CB 1954 or product formation was the same when the co-factor was either NAD(P)H or NADH and when the reduction was performed under helium.

To show that the nitroreductase was producing a cytotoxic species, the reduction of CB 1954 was carried out in the presence of V79 cells, which are insensitive to CB 1954. As shown in Table 4, a dramatic cytotoxic effect was observed in Hamster V79 cells—but only under those conditions in which the nitroreductase reduced CB 1954.

TABLE 4

The effect of CB 1954 on the survival of V79 cells in the presence of the E. coli B nitroreductase. All treatments were for 2 hours at 37° C. and the cells were then plated out for their resulting colony-forming ablity. The nitroreductase concentration was 2 µg/ml and NADH was used as a cofactor.

| TREATMENT | % SURVIVAL | % DRUG REDUCTION |
|---|---|---|
| CONTROL | 100 | — |
| + 500 µM NADH | 100 | — |
| + 50 µM CB 1954 | 100 | <1.0 |
| + NADH + CB 195 | 41 | <1.0 |
| + Nitroreductase (NR) | 94 | — |
| + NR + 50 µM CB 1954 | 99 | <1.0 |
| + NR + CB 1954 + 500 µM NADH | 0.024 | 72 |

EXAMPLE 3

Substrate specificity of the E. coli nitroreductase enzyme

The ability of the E. coli nitroreductase of the invention to reduce nitro-compounds other than CB 1954 was determined by HPLC by following the decrease in the peak area of NADH resulting from its oxidation. The experiments were carried out as above but the aliquots were injected onto a Partisphere SAX (110×4.7 mm) HPLC column and eluted isocratically (1 ml/min) with 75 nM NaH$_2$PO$_4$. The results are shown in Table 5.

TABLE 5

The relative rates of reduction of various nitrobenzamides and nitrobenzenes with *E. coli* nitroreductase enzyme. Reduction rates were determined by the resulting oxidation of NADH. All reactions were carried out at 37° C. in air, with NADH (500 μM) as electron donor, at an initial substrate concentration of 100 μM.

| SUBSTRATE | RELATIVE RATE OF NADH OXIDATION NR |
|---|---|
| CB 1954 | 1.0 |
| 2,4-dinitro-5-(2-hydroxy-ethylamino)benzamide | 0.04 |
| 2-amino-5-(aziridin-1-yl)-4-nitrobenzamide | <0.01 |
| 4-amino-5-(aziridin-1-yl)-4-nitrobenzamide | <0.01 |
| 5-chloro-2,4-dinitrobenzamide | 22.4 |
| 3,5-dinitrobenzamide | 75.5 |
| 2-nitrobenzamide | 0.06 |
| 3-nitrobenzamide | 1.8 |
| 4-nitrobenzamide | 5.1 |
| 2,4-dinitrophenol | <0.01 |
| 5-nitro-2-furaldehydesemicarbazone (nitrofurazone) | 3.6 |

EXAMPLE 4
Enzyme Kinetic and Inhibition Studies

Quinone reductase activities were assayed by a spectrophotometric method using menadione as a substrate and cytochrome c as a terminal electron acceptor as described in Knox et al. Biochem. Pharmacol., 37, 4671–4677, 1988. Initial rates of reaction were determined by linear regression analysis (r>0.995) and kinetic parameters determined from the resulting plots as described by Roberts et A. Biochem. Pharmacol. 38, 4137–4143, 1989. Protein concentration was determined using the a conventional protein assay (Bio-Rad) calibrated against bovine serum albumin.

Kinetic parameters for the *E. coli* nitroreductase and Walker NAD(P)H, dehydrogenase (quinone) EC. 1.6.99.2, are given in Table 6. Although both enzymes have comparable Km's for CB 1954, the Km of the nitroreductase for NADH is about 10 fold less than the Walker enzyme. The absolute rates of reduction of CB 1954 (i.e. under saturating conditions) by the two enzymes is their kit values and this is 90 fold higher for the *E. coli* nitroreductase. Menadione was also a substrate for both enzymes with little difference in their respective $k_{cat}$'s although the Km of nitroreductase for this substrate was 60 fold higher.

Dicoumarol was an inhibitor of the nitroreductase. No kinetic parameters could be measured with respect to NADH. With respect to menadione, dicoumarol was an uncompetitive inhibitor with a Ki' of 1.90±0.38 μM.

TABLE 6

Kinetic parameters for the *E. coli* B nitroreductase and Walker NAD(P)H dehydrogenase (quinone).

| COMPOUND | | NR | WALKER |
|---|---|---|---|
| NADH | Km | ~6 μM | 75 μM |
| CB 1954 | Km | 862 ± 145 μM | 826 ± 46 μM |
|  | $K_{cat}$ | 360 min$^{-1}$ | 4 min$^{-1}$ |
| MENADIONE | km | 80 μM | 1.3 μM |
|  | $K_{cat}$ | 4.2 × 10$^4$ min$^{-1}$ | 6.5 × 10$^4$ min–1 |

EXAMPLE 5

The ability of the *E. coli* B nitroreductase to activate compounds other than CB 1954 to a cytotoxic species.

As shown in Table 7, a large cytotoxic effect was observed in human MAWI cells by the prodrugs CB 1837 and CB 10-107 but only under those conditions when the prodrug was reduced by the nitroreductase enzyme.

TABLE 7

The effect of enzyme-activated prodrugs on the survival of MAWI cells. 1 ml volumes of MAWI cells (2 × 10$^5$/ml were incubated with 50 μM prodrug, 500 μM NADH, and 10 μg/ml the enzyme of Example 1. After a 2 hour incubation at 37° C., the cells were harvested and assayed for their colony forming ability, and the supernatant assayed for the concentration of remaining prodrug by HPLC.

| TREATMENT | % SURVIVAL | % DRUG REDUCTION |
|---|---|---|
| CONTROL | 100 | — |
| +500 μM NADH | 100 | — |
| +50 μM CB 1837 | 97.4 | <1.0 |
| +NADH + CB 1837 | 97.4 | <1.0 |
| +50 μM CB 10-107 | 85.6 | <1.0 |
| +NADH + CB 10-107 | 87.9 | <1.0 |
| +NR + CB 1837 + 500 μM NADH | 1.56 | >95 |
| +NR + CB 10-107 + NADH | 5.0 | 45 |

EXAMPLE 6

PREPARATION OF 1,4-DIHYDRO-NICOTINIC ACID RIBOSIDE FROM EITHER NICOTINIC ACID RIBOSIDE OR NICOTINIC ACID RIBOTIDE (i) Preparation of nicotinic acid riboside from nicotinic acid ribotide A solution of nicotinic acid ribotide (nicotinic acid mononucleotide) (Sigma, Poole, U.K.) (25 mg) in aqueous buffer (tris 100 mM; pH 8.5; MgCl$_2$; 2.5 ml), was treated with 2000 units of alkaline phosphatase, type VII-S (100 μl; 20,000 units/ml) (Sigma) at 37° C. for 1 hour. The alkaline phosphatase was separated from the digest by centrifugal molecular filtration (10,000 molecular weight limit; "Centricon 10"; Amicon, High Wycombe, U.K.). Dilutions (1:100) of the solution were analysed both before and after digestion with alkaline phosphatase by anion exchange high performance liquid chromatography (Partisphere 5-SAX column, eluted isocratically with 0.1M NaH$_2$PO$_4$, pH5, 1.5 ml/min, 10 μl injection volume, monitored by UV absorbance at 260 nm). The parent compound eluted with a retention time of 1.18 minutes. Post digestion examination indicated that a complete conversion had occurred to give the novel title compound eluting with a retention time of 0.63 minutes, taken to be indicative of dephosphorylation, yielding the riboside.

(ii) Reduction of nicotinic acid riboside to 1,4-dihydronicotinic acid riboside

The method of Jarman and Searle (1972) was adopted. The method was applied both to nicotinic acid riboside as produced above, and also to chemically synthesised material (Jarman 1969). Identical results were obtained with starting compound from either source of origin.

To an aqueous solution of nicotinic acid riboside (5 ml; 4 mg/ml) was added 50 mg sodium carbonate, 50 mg sodium bicarbonate, and 50 mg sodium hydrosulphite. The stoppered solution was incubated at 37° C. for 1 hour and the reduction product separated by preparative reverse phase HPLC. The 5 ml was injected onto a microsorb 5 μm C18 (10×250 mm) reverse-phase column (Rainin) and eluted by a gradient of methanol in water (0–100% over 30 minutes) buffered at pH 5 by 10 mM NH$_4$CH$_3$COO at 4 ml/min. The eluate was continuously monitored both by UV absorbance and by fluorescence and the reduction product, (chromatographing with baseline resolution at a retention time of 12–13 minutes), was characterised by both its absorbance maximum at 326 nm (at pH5; 340 nm at pH7) and by its fluorescence (Gilson 121 fluorometer with wide band glass filters; excitation centred at 350 nm; emission at 450 nm), neither of which properties are displayed by the parent compound. Eluates of 4 ml. of a 2 mM solution (assuming an $\epsilon_{340}$ of 6200 (i.e. the same as NADH) were typical, indicating a yield of 2.7 mg i.e. approximately 13%. Prior to experimental usage, the preparations were analysed by analytical HPLC and confirmed to be essentially pure.

References:

(i) M. Jarman and F. Searle. Potential Coenzyme Inhibitors-V. Biochem. Pharmacol. Vol 21, pp. 455–464, 1972.

(ii) M. Jarman. 4-Substituted Nicotinic acids and Nicotinamides. Part III. Preparation of 4-Methylnicotinic acid Riboside. J. Chem. Soc. (C), 918–920, 1969.

EXAMPLE 7

The ability of 1,4-dihydro-nicotinic acid riboside to act as a cofactor for the *E. coli* nitroreductase.

The ability of the nitroreductase enzyme to be able to use a synthetic cofactor in place of NADH or NADPH for the reduction of CB 1954 is shown in FIG. 1. The nitroreductase enzyme can use both 1,4-dihydro-nicotinic acid riboside and NADH with equal efficiency as cofactors for the reduction of CB 1954. In contrast Walker DT diaphorase cannot utilise this synthetic cofactor. Therefore 1,4-dihydro-nicotinic acid riboside is a selective cofactor for the *E. coli* nitroreductase enzyme and cannot be used by mammalian DT diaphorase.

In the following Examples 8–12, "Silica gel" refers to Merck silica gel 60, 70–230 mesh and Proton NMR spectra were obtained at 300 MHz in $CDCl_3$. Temperatures are in °C.

EXAMPLE 8

4-(Bis(2-chloroethyl)amino]phenylcarbamic acid 4'-nitrobenzyl ester

To a stirred solution of 4-nitrobenzyl chloroformate (295 mg) in dry $CHCl_3$ (5 ml), a solution of 4-[bis(2-chloroethyl)amino]aniline hydrochloride (367 mg and $NEt_3$ (377 µl) in dry $CHCl_3$ (5 ml) was added over 5 min. After 1 hr the solution was kept at 20° for 18 hr, then evaporated. The residue was chromatographed on a column of silica gel with $CHCl_3$ to give the title product as a yellow solid which recrystallized from benzene/petroleum ether as prisms, m.p. 111°–112°. Yield, 361 mg (64%). Chemical ionization mass spectrum with $CH_4$: ion at m/z 412 (M+1, relative intensity 1.00) indicates M=411. $C_{18}H_{19}N_2O_4Cl_2$ requires M=411 (for $Cl^{35}$ isotope). NMR: δ3.57 (m, 4H, $CH_2Cl$ or $CH_2N$), 3.69 (M, 4H, $CH_2Cl$ or $CH_2N$), 5.28 (s, 2H, $ArCH_2$), 6.65 (d, 4H, ArH), 7.51 (d, 2H, ArH) and 8.23 (d, 2H, ArH).

EXAMPLE 9

4-[Bis(2-chloroethyl)amino]phenyl 4'-nitrobenzyl carbonate

A solution of 4-nitrobenzyl chloroformate (58 mg) in dry $CHCl_3$ (1.5 ml) was added to a stirred, ice-cooled solution of 4-[bis(2-chloroethyl)amino]-phenol hydrochloride (72 mg) and $NEt_3$ (74 µl) in dry $CHCl_3$ (2 ml). After 18 hr at 21°, the solution was evaporated and the residue chromatographed on a column of silica gel with $CHCl_3$/petroleum ether (3:2) to give the title compound which crystallized from ETOAc/petroleum ether as pale yellow prisms, m.p. 77°–79° (yield, 102 mg). FAB MS: ion at m/z 413 indicates M=412 ($C_{18}H_{18}N_2O_5Cl_2$ requires M=412).NMR ($CDCl_3$): δ3.62 (m, $NCH_2$ or $ClCH_2$), 3.69 (m, $NCH_2$ or $ClCH_2$), 5.33 (s, $ArCH_2$), 6.64 (d, ArH), 7.05 (d, ArH), 7.59 (d, ArH) and 8.25 (d, ArH).

EXAMPLE 10

N-4-Nitrobenzyloxycarbonyl-actinomycin D

Actinomycin D (AMD, 41 mg) in MeOH (5 ml) was hydrogenated over 10% Pd/C for 2 hr, then evaporated in vacuo. The residue under $N_2$ was dissolved in a solution of 4-nitrobenzyl chloroformate (18 mg) in dry $CHCl_3$ (1.5 ml) and a solution of $NEt_3$ (10 µl) in $CHCl_3$ (1.5 ml) was then added. After stirring under $N_2$ for 24 hr, the catalyst was filtered off and the solution, after dilution with MeOH (200 ml), was aerated for 3 days. The solution was evaporated and the product was purified to remove AMD by semi-preparative HPLC twice on a 1 cm diameter column of reversed-phased $C_{18}$-bonded silica with a 50–100% gradient of MeCN in $H_2O$. The title compound was crystallised from ethyl acetate/petroleum ether as red prisms. Yield, 31 mg (66%). Electrospray mass spectrum: ions at m/z 1434.5 (M+H) and 1456.4 (M+Na) indicates M=1433.5. $C_{70}H_{91}N_{13}O_{20}$ (lowest mass isotope) requires M=1433.65. NMR gave the same signals as AMD plus δ6.71 (d, 1H, $ArCH_2$), 7.09 (d, 1H, $ArCH_2$) and additional signals in the aromatic region.

EXAMPLE 11

N-4-nitrobenzyloxycarbonyl-doxorubicin VI

Doxorubicin hydrochloride (2.25 mg) was dissolved in dimethylformamide (DMF) (0.3 ml) containing triethylamine ($NEt_3$) (0.55 µl) and a solution of 4-nitrobenzyl-4'-nitrophenylcarbonate (1.4 ml) in DMF (0.1 ml) was added. After stirring in the dark for 3 days, the mixture was separated by HPLC on a column (1 cm. diam.) of $C_{18}$ reversed-phase silica with a gradient of 25 to 100% MeCN in 0.01M formate buffer (pH 4.0). The principal red fraction was concentrated and rechromatographed with $H_2O$ in place of the formate buffer. Evaporation in vacuo afforded the product (2.1 mg) as an amorphous red powder. Electrospray MS: ion at 723 (M+H) indicates M=722. $C_{35}H_{34}N_2O_{15}$ requires M=722.

EXAMPLE 12

N-4-Nitrobenzyloxycarbonyl-mitomycin C

A solution of mitomycin C (36 mg) in dimethyl formamide (DMF) (2 ml) containing $NEt_3$ 14 µl) was added to 4-nitrobenzyl chloroformate (30 mg) and the mixture was stirred at 21° for 4 hr. After evaporation in vacuo, the residue was chromatographed on a column of silica gel with EtOAc to give the title compound as a dark red solid (49 mg). Electrospray MS: ion at 514 (M+H) indicates M=513. $C_{23}H_{23}N_5O_9$ requires M=513.

EXAMPLE 13

Formation of actinomycin D by the action of the nitroreductase upon prodrug V (100 µM) and cofactor (500 µM NADH) were incubated with enzyme (2 µg/ml *E. coli* B nitroreductase of Example 1 in 10 mM sodium phosphate buffer (pH7) in air at 37° C. At various times, aliquots (20 µl) were injected onto a Microsorb C18 reverse-phase (240×4.7 mm) HPLC column and eluted isocratically (1 ml/min) with 80% acetonitrile in water. The eluate was continuously monitored for absorption at 280 nm and the concentration of drug calculated by integration of the peak corresponding to this compound on the HPLC trace. Only when the enzyme was present was actinomycin D released from the prodrug.

Figure 2:
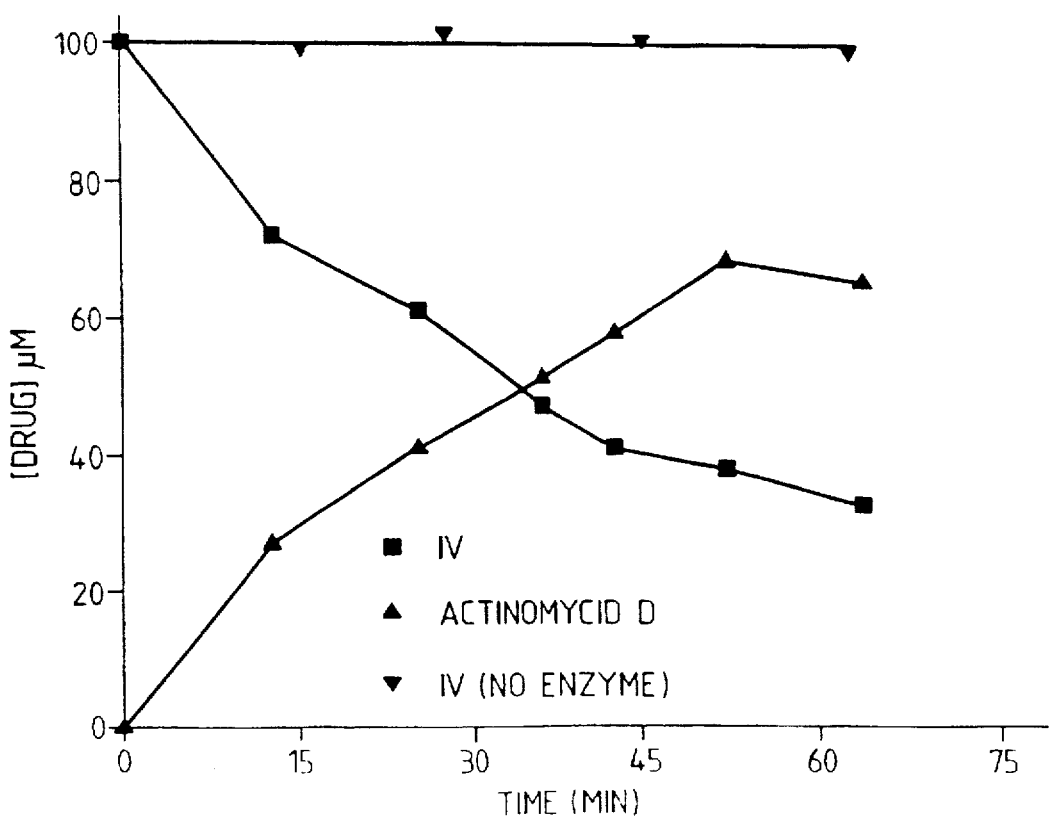
FIG. 2 shows the formation of actinomycin D (AMD) during incubation of an AMD prodrug with a nitroreductase of the present invention.

Disappearance of the prodrug N-4-nitrobenzyloxycarbonyl-actinomycin D (V) and formation of actinomycin D during incubation with the *E. coli* B nitroreductase of Example 1 is shown in FIG. 2.

EXAMPLE 14

The formation of mitomycin C by the action of the nitroreductase enzyme upon Prodrug VII Prodrug VII (100 μM) and cofactor (500 μM NADH) were incubated with enzyme (5 μg/ml *E. coli* B nitroreductase of Example 1) in 10 mM sodium phosphate buffer (pH7) in air at 37° C. At various times aliquots (10 μl) were injected onto a Partisphere C18 reverse-phase (150×4.7 mm) HPLC column and eluted isocratically (2.0 ml/min) with 50% methanol in water. The eluate was continuously monitored for absorption at 260 and 340 nm and the concentration of the drugs calculated by integration of the peak corresponding to the compound on the HPLC trace.

Figure 3:
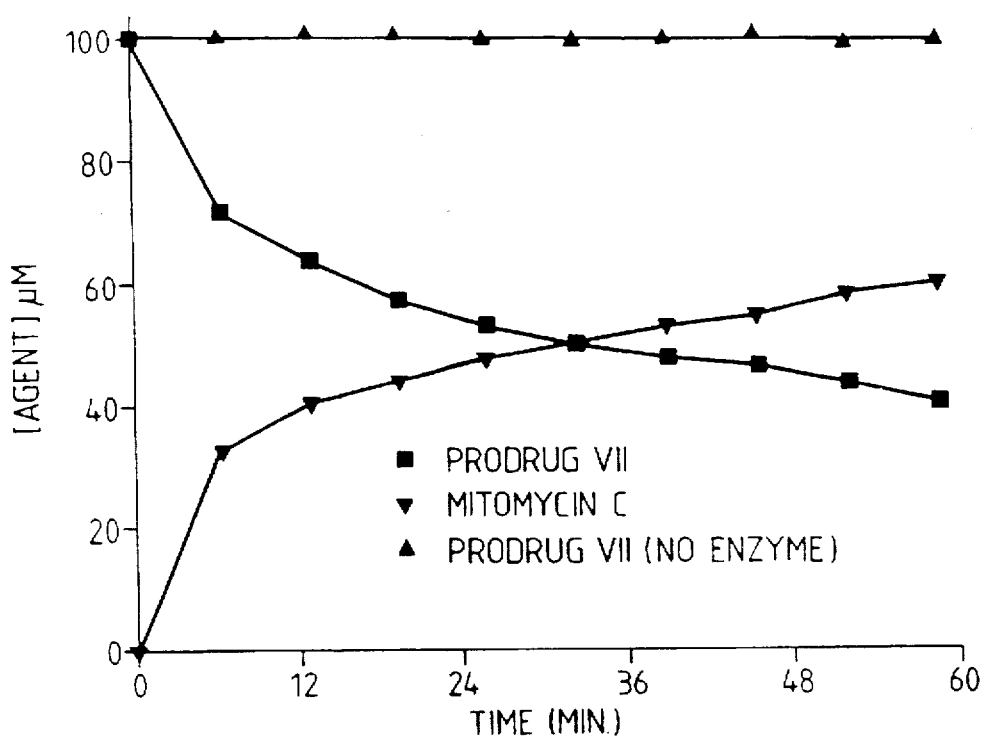
FIG. 3 shows the formation of mitomycin C (MC) during incubation of an MC prodrug with a nitroreductase of the present invention.

Disappearance of prodrug VII and the formation of mitomycin C during this incubation is shown in FIG. 3. Only in the presence of the enzyme is mitomycin C released from the prodrug.

EXAMPLE 15

Activation of prodrug I where $R^1NH_2$=III and prodrug V by the nitroreductase

Generation of cytotoxicity by the action of the *E. coli* nitroreductase of Example 1 upon the prodrugs 4-[bis(2-chloroethyl)amino]phenylcarbamic acid 4'-nitrobenzyl ester (I where $R^1NH_2$=I) and N-4-nitrobenzyloxy-carbonyl-actinomycin D (v) are shown in Table 8.

TABLE 8

The effect of enzyme-activated prodrugs on the survival of V79 cells. 1 ml volumes of V79 cells (2 × 10⁵/ml) were incubated with prodrug, 500 μM NADH, and 10 μg/ml enzyme. After a 2 hour incubation at 37° C., the cells were harvested and assayed for their colony forming ability, and the supernatant assayed for the concentration of remaining prodrug by HPLC.

| TREATMENT | (%) SURVIVAL | % DRUG REDUCTION |
|---|---|---|
| CONTROL | 100 | — |
| +500 μM NADH | 100 | — |
| +50 μM (I where $R^1NH_2$ = III) | 27.1 | <1.0 |
| +NR + 50 μM (I where $R^1NH_2$ = III) + 500 μM NADH | .0.001 | 30 |
| +1 μM V | 98.3 | <1.0 |
| +10 μM V | 39.3 | <1.0 |
| +NR + μM V + 500 μM NADH | 27.4 | 90.5 |
| +NR + 10 μM V + 500 μM NADH | .0.0001 | 93 |
| +NR + CB 10-107 + NADH | 5.0 | 45 |

EXAMPLE 16

Preparation and binding of Antibody: Enzyme Conjugate

Antibody:enzyme conjugate of A5B7 F(ab)₂: nitroreductase was prepared using the heterobifuncitional agents succinimidyl 4-(p-maleimidophenyl)butyrate (SMPB) to insert active maleimide groups into the immunoglobulin, and 2-mercapto-[S-acetyl]acetic acid N-hydroxysuccinimide (SATA) to thiolate the *E. coli* nitroreductase. On mixing the proteins the maleimide groups react with thiols to form a thioether bond. The molar ratio of SMPB:immunoglobulin used was 10:1 and the molar ratio of SATA:nitroreductase was 4:1. Antibody:enzyme conjugate thus prepared was isolated from high molecular weight aggregates and uncoupled components by gel filtration chromatography using a calibrated column (16×700 mm) of Superdex G200. The column was equilibrated in phosphate buffered saline (PBS) and eluted with the same buffer at a flow rate of 1.0 ml/min. Fractions containing material corresponding in molecular weight to 2:1 and 1:1 conjugate (316 KDa and 233 KDa respectively) were pooled and rechromatographed on the same column and samples from pooled fractions were run on 4–15% SDS-PAGE gels (Pharmacia Phastgels, run for 60 vh) under non-reducing conditions together with calibration proteins. The conjugate was present as material with Mr 125 KDa (corresponding to 1:1 F(ab')₂:nitroreductase and higher molecular weight conjugates together with less amounts of free F(ab')₂ and nitroreductase.

Figure 4:
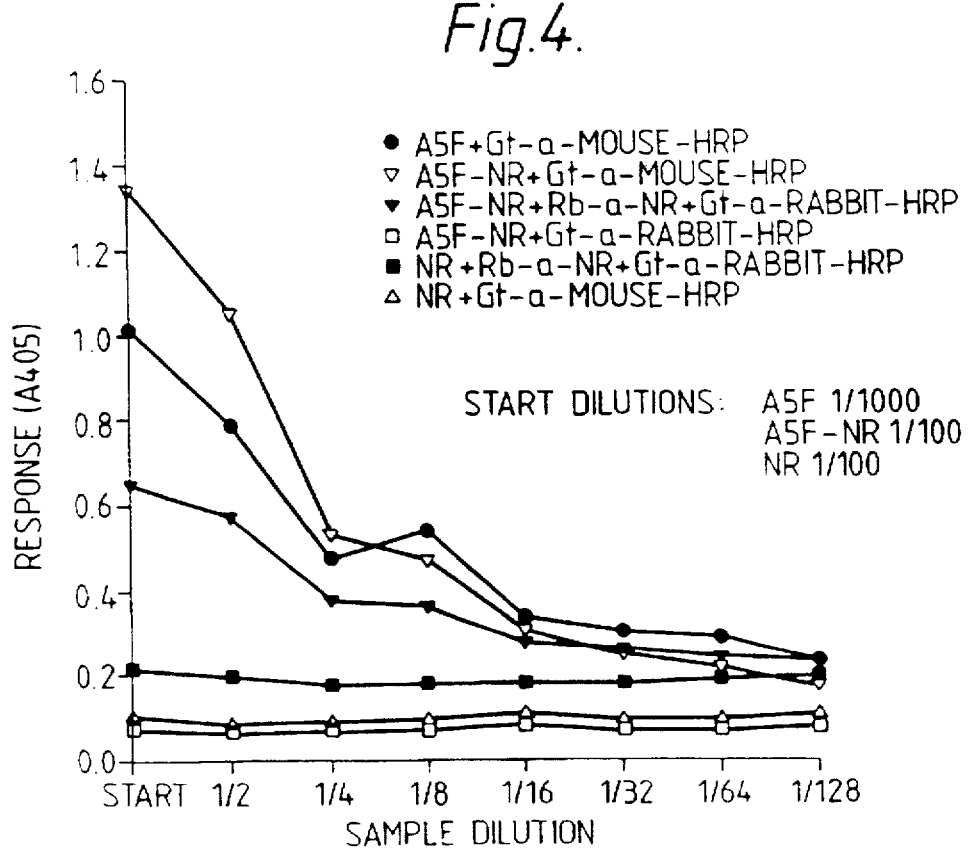
FIG. 4 shows the binding in vitro of an antibody-enzyme conjugate according to the invention to cells.

The enzymic activity of the conjugate was established by the routine assay using CB1954 as substrate. The conjugate was shown to bind to plates coated with 1 μg/ml CEA antigen and to contain binding sites for both rabbit anti-mouse immunoglobulin and rabbit anti-nitroreductase secondary antibodies (FIG. 4). Samples of uncoupled F(ab')₂ and nitroreductase were used to confirm the specificity of the secondary antibody binding.

The antibody binding was determined using a standard horse radish peroxidase (HRP) colorimetric ELISA assay, with the results being read at 405 nm. The inverted open triangles on FIG. 4 show that bound A5B7 F(ab')₂-nitroreductase conjugate can be detected with a goat anti-mouse immunoglobulin antibody, and the closed inverted triangles show that the conjugate is also detected by a rabbit anti-NR antibody (the anti-NR antibody being detected via the use of a goat anti-rabbit immunoglobulin antibody. The controls shown in FIG. 4 are: closed circles=binding of unconjugated A5B7 F(ab')₂; open squares=A5B7 F(ab')₂-NR conjugate detected with goat anti-rabbit immunoglobulin; closed squares=NR only detected with rabbit anti-NR; open triangles=NR only detected with goat anti-mouse immunoglobulin.

EXAMPLE 17

In vivo toxicity of prodrug

The actinomycin D prodrug (AMDPD) of formula V was tested for toxicity in mice. Groups of 3 mice were given 1, 10 or 100 mg/kg body weight i.p. of AMPD, and two further groups of 3 mice were given 1 and 10 mg/kg body weight i.p. of actinomycin D (AMD) dissolved in arachis oil. A further group of 3 mice were untreated, and a final group of 3 mice were given arachis oil i.p. only.

The body weight of the mice were monitored over 9 days. The results are shown on Table 9. All mice treated with 10 mg/kg of AMD were dead by day 1. A similar result was obtained with a dose of 5 mg/kg. These data indicate that AMDPD is at least 20 to 100 fold less toxic than AMD. In practice, the toxicity of AMDPD is likely to be even lower, since the preparation of AMDPD used contains about 1% unconverted AMD.

TABLE 9

Toxicity of AMD and AMDPD

| Compound | Dose | Weight as % of Day 0 | | | |
|---|---|---|---|---|---|
| | | Day 2 | Day 3 | Day 7 | Day 9 |
| Prodrug | 100 | 96.4 (1 dead) | 95.6 | 95 | 96 |
| | 10 | 109 | 105 | 108 | 110 |
| | 1.0 | 102 | 101 | 101 | 103 |
| Active Drug | 10 | All dead on day 1. | | | |
| | 1.0 | 98.6 | 95 | 101.6 | 103 |
| Control | — | 104 | 103 | 106 | 106 |
| Oil | | 99 | 99 | 101 | 102 |

What is claimed is:

1. A compound of the formula (I):

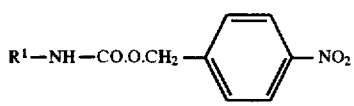

I where $R^1$ is a group such that the compound $R^1NH_2$ represents a nitrogen mustard of the formula (IV):

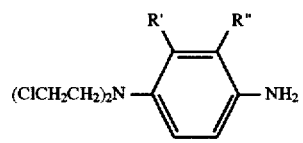

IV where R' and R" are H, F, or $CH_3$.

2. A compound of the formula (II):

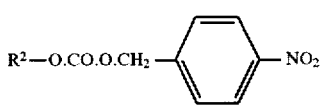

where $R^2$ is a group such that the compound $R^2OH$ is a phenolic nitrogen mustard.

3. A compound according to claim 1 where R' and R" are both hydrogen.

4. A compound according to claim 2 of the formula (VIII):

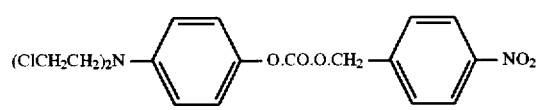

5. A compound of the formula (V), (VI), (VII):

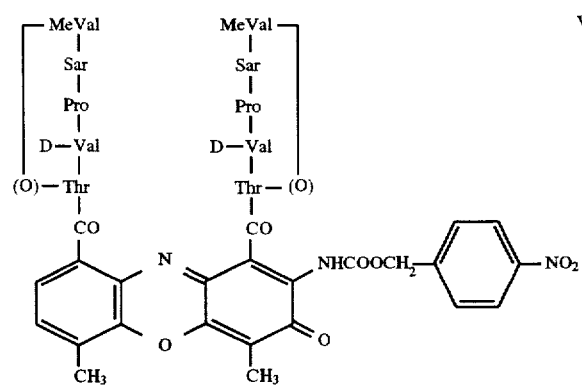

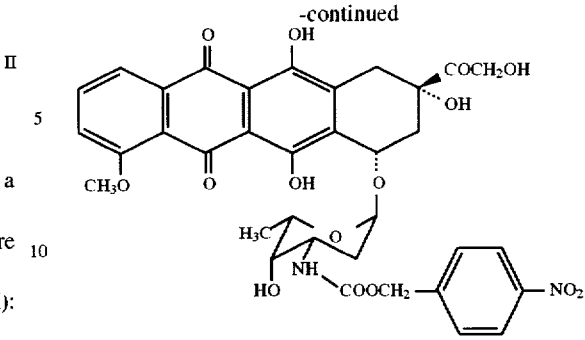

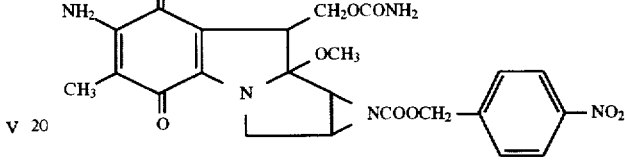

6. A process for the production of a prodrug of formula (I) as defined in claim 1 which comprises reacting a nitrogen mustard of the formula (IV) with 4-nitrobenzyl chloroformate under anhydrous conditions.

7. A process for the production of a prodrug of formula (II) as defined in claim 2 which comprises reacting a phenolic nitrogen mustard with 4-nitrobenzyl chloroformate under anhydrous conditions.

8. A process for the production of a prodrug of formula (V), (VI), or (VII) as defined in claim 5 which comprises reacting actinomycin D, doxorubicin, or mitomycin C, respectively, with 4-nitrobenzyl chloroformate under anhydrous conditions.

* * * * *